United States Patent [19]

Saji et al.

[11] 4,288,448
[45] Sep. 8, 1981

[54] N-SUBSTITUTED IMIDAZOLE DERIVATIVES, AND THEIR USE

[75] Inventors: Ikutaro Saji; Shunji Aono, both of Osaka; Takao Okuda; Hideo Agui, both of Sonehigashi, all of Japan

[73] Assignee: Sumitomo Chemical Company, Limited, Osaka, Japan

[21] Appl. No.: 210,619

[22] Filed: Nov. 26, 1980

[30] Foreign Application Priority Data

Dec. 5, 1979 [JP] Japan .................. 54-158581

[51] Int. Cl.³ .............. A61K 31/415; A61K 31/495; C07D 403/00; C07D 405/14
[52] U.S. Cl. ................. 424/273 R; 424/250; 548/336; 544/370
[58] Field of Search .......... 548/336; 424/273 R, 424/250; 544/370

[56] References Cited

U.S. PATENT DOCUMENTS

| | | | |
|---|---|---|---|
| 3,468,902 | 9/1969 | Gamaliel Beaman et al. | 548/336 |
| 3,493,582 | 2/1970 | Hoffer | 548/336 |
| 3,705,172 | 12/1972 | Buchel et al. | 548/345 |
| 3,705,172 | 12/1972 | Buchel et al. | 548/345 |

OTHER PUBLICATIONS

Godefroi et al., J. Med. Chem., 12, 784–791, 1969.
J. Med. Chem., 12, 784–791 (1969).

*Primary Examiner*—Henry R. Jiles
*Assistant Examiner*—Jane T. Fan
*Attorney, Agent, or Firm*—Birch, Stewart, Kolasch & Birch

[57] ABSTRACT

An N-substituted imidazole compound of the formula:

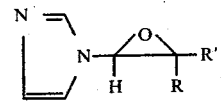

wherein R and R' are independently a phenyl group optionally substituted with one or more halogen, $C_1$–$C_8$ alkyl, $C_1$–$C_8$ alkoxy, $C_1$–$C_8$ alkylthio, phenyl, phenoxy, phenylthio, hydroxyl, trifluoromethyl, amino, carbamoyl, di($C_1$–$C_8$) alkylamino, $C_1$–$C_8$ alkanoylamino, nitro, cyano, carboxy, $C_1$–$C_8$ alkoxycarbonyl, $C_1$–$C_8$ alkylsulfonyloxy or $C_1$–$C_8$ alkanoylpiperazino groups; a $C_1$–$C_{15}$ alkyl group or a phenyl ($C_1$–$C_2$) alkyl group optionally bearing halogen on the benzene ring, and its acid-addition salts, which is useful as an antifungal agent.

18 Claims, No Drawings

N-SUBSTITUTED IMIDAZOLE DERIVATIVES, AND THEIR USE

The present invention relates to N-substituted imidazole derivatives, and their production and use. More particularly, it relates to N-substituted imidazole compounds of the formula:

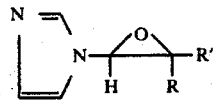 (I)

wherein R and R' are independently a phenyl group optionally substituted with one or more halogen, $C_1-C_8$ alkyl, $C_1-C_8$ alkoxy, $C_1-C_8$ alkylthio, phenyl, phenoxy, phenylthio, hydroxyl, trifluoromethyl, amino, carbamoyl, di($C_1-C_8$)alkylamino, $C_1-C_8$ alkanoylamino, nitro, cyano, carboxy, $C_1-C_8$ alkoxycarbonyl, $C_1-C_8$ alkylsulfonyloxy or $C_1-C_8$ alkanoylpiperazino groups; a $C_1-C_{15}$ alkyl group or a phenyl($C_1-C_2$)alkyl group optionally bearing halogen on the benzene ring, and their acid-addition salts, and their preparation process and their antifungal use.

In the above significances, the $C_1-C_8$ alkyl moiety may be straight or branched and can cover methyl, ethyl, n-propyl, isopropyl, n-butyl, isobutyl, t-butyl, n-pentyl, n-hexyl, n-heptyl, n-octyl, etc. Among them, those having 1 to 4 carbon atoms are preferred. The $C_1-C_8$ alkanoyl moiety may be also straight or branched and can cover formyl, acetyl, propionyl, butyryl, hexanoyl, etc. Among them, those having 1 to 4 carbon atoms are favorable. Examples of the $C_1-C_{15}$ alkyl group include n-nonyl, n-decyl, n-undecyl, n-dodecyl, n-tridecyl, n-tetradecyl and n-pentadecyl in addition to the $C_1-C_8$ alkyl moieties as specifically mentioned above. The number of the substituent(s) which may be present on the phenyl group or the benzene ring is usually not more than 3.

The said N-substituted imidazole compound (I) can be prepared, for instance, by reacting imidazole or its functional derivative of the formula:

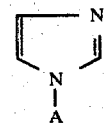 (II)

wherein A is a hydrogen atom, a trialkyltin group (e.g. tributyltin) or a trimethylsilyl group, with an aldehyde of the formula:

$$\mathrm{OHC-\underset{\underset{R}{\mid}}{\overset{\overset{Z}{\mid}}{C}}-R'} \qquad (III)$$

wherein Z is a halogen atom and R and R' are each as defined above.

The imidazole and its functional derivatives (II) are known and described, for example, in Chem. Ber., Vol. 93, 2804 (1960) and Rec. Trav. Chim., Vol. 81, 202 (1962). The aldehyde (III) is known or can be easily prepared by a per se known procedure as described in J. Am. Chem. Soc., Vol. 87, 827 (1965), J. Org. Chem., Vol. 37, 1956 (1972), Chem. Ber., Vol. 106, 2610 (1973), Chem. Letters, 995 (1977), etc.

The reaction is usually carried out by treating imidazole or its functional derivative (II) with the aldehyde (III) in a molar proportion of 1–3:1 in an inert solvent. Examples of the inert solvent are an alkanol (e.g. methanol, ethanol), an ether (e.g. tetrahydrofuran, dioxane), a hydrocarbon (e.g. hexane, benzene, toluene, xylene), a halogenated hydrocarbon (e.g. chloroform, methylene chloride), acetonitrile, dimethylformamide, dimethylsulfoxide, acetone, etc. The reaction temperature is normally from 0° C. to the boiling temperature of the solvent, preferably from room temperature (e.g. 5° C.) to the refluxing temperature of the reaction system.

Examples of the acid-addition salts of the N-substituted imidazole compound (I) are the hydrochloride, hydrobromide, phosphate, nitrate, acetate, maleate, succinate, fumarate, tartrate, citrate, salicylate, sorbate, lactate, etc. Those acid-addition salts may be prepared by a per se conventional procedure.

The N-substituted imidazole derivatives of the invention are novel and exhibit a strong antifungal activity against pathogenic fungi as shown in Table 1. Some of them show anti-mold activity as well as antifungal activity.

TABLE 1

| | | | Minimum inhibitory concentration (µg/ml)*[(1)] | |
|---|---|---|---|---|
| R | R' | Form | Candida albicans | Trichophyton rubrum |
| 2-Cl-C₆H₄ | C₆H₅ | Free | 10 | 1.25 |
| 2,4-Cl₂-C₆H₃ | C₆H₅ | Free | 10 | 1.25 |

TABLE 1-continued
Antifungal activity in vitro

N-Substituted imidazole derivative (I)

| R | R' | Form | Minimum inhibitory concentration (μg/ml)*[1] Candida albicans | Trichophyton rubrum |
|---|---|---|---|---|
| 2,4-diCl-C6H3 | 2,4-diCl-C6H3 | Free | 20 | 0.6 |
| 2-Cl-C6H4 | 2,4-diCl-C6H3 | Hydrochloride | 5 | 1.25 |
| 2-Cl-C6H4 | 4-F-C6H4 | Nitrate | 5 | 0.6 |
| 2,4-diBr-C6H3 | C6H5 | Free | 2.5 | 1.25 |
| 2-Cl-6-F-C6H3 | C6H5 | Nitrate | 10 | 0.6 |
| 2-Cl-C6H4 | 3-CH3O-C6H4 | Nitrate | 10 | 1.25 |
| 2-I-C6H4 | 4-I-C6H4 | Oxalate | 10 | 1.25 |
| 2-Cl-6-F-C6H3 | 4-Cl-C6H4 | Nitrate | 5 | 0.6 |
| 2,4-diCl-C6H3 | 2-Cl-C6H4 | Free | 5 | 0.6 |
| 2,4-diCl-C6H3 | 4-Cl-C6H4 | Nitrate | 5 | 1.25 |
| 3,4-diF-C6H3 | C6H5 | Oxalate | 20 | 2.5 |
| 2,4-diCH3-C6H3 | C6H5 | Nitrate | 20-100 | 10 |
| 2-Cl-C6H4 | 3-CF3-C6H4 | Nitrate | 20 | 10 |
| 4-Cl-C6H4 | 4-CH3OOC-C6H4 | Nitrate | 20-100 | 20-100 |
| 2-Cl-C6H4 | 4-C6H5-C6H4 | Oxalate | 20-100 | 2.5 |
| 2,4-diI-C6H3 | C6H5 | Free | 20-100 | 20 |

TABLE 1-continued

Antifungal activity in vitro

N-Substituted imidazole derivative (I)

$$\underset{H}{\underset{|}{N}} \diagdown N - \underset{R}{\underset{|}{C}} - \underset{}{\overset{O}{\diagup\diagdown}} - R'$$

| R | R' | Form | Minimum inhibitory concentration (μg/ml)*[1] | |
|---|----|------|---------------------------------------------|---|
| | | | Candida albicans | Trichophyton rubrum |
| 2-Cl-C6H4- | 2-Cl-C6H4- | Free | 10 | 5 |
| 2-Cl-C6H4- | 4-Cl-C6H4- | Free | 20-100 | 10 |
| C6H5- | C6H5- | Free | >100 | 20-100 |
| 4-Cl-C6H4- | 4-Cl-C6H4- | Free | 20 | 10 |
| 4-Cl-C6H4- | C6H5- | Free | 20-100 | 5 |
| 4-O2N-C6H4- | C6H5- | Free | >100 | 20 |
| 2-Cl-C6H4- | 4-(C6H5-O-)C6H4- | Oxalate | >100 | 20 |
| 2-Cl-C6H4- | 4-(C6H5-S-)C6H4- | Hydrochloride | >100 | 20-100 |
| 4-Cl-C6H4- | 4-HOOC-C6H4- | Free | 20-100 | 20 |
| 4-Cl-C6H4- | 4-H2NCO-C6H4- | Free | >100 | >100 |
| 2-Cl-C6H4- | 4-[CH3CO-N(piperazine)N-]-C6H4- | Free | >100 | >100 |
| 3,4-Cl2-C6H3- | CH3 | Nitrate | 20-100 | 2.5 |
| 3,4-Cl2-C6H3-*[2] | (n)C6H13 | Oxalate (M.P., 124-127° C.) | 5 | 2.5 |
| 3,4-Cl2-C6H3-*[3] | (n)C6H13 | Oxalate (M.P., 138-140° C.) | 5 | 5 |
| C6H5- | 2,4-Cl2-C6H3-CH2- | Nitrate | 20-100 | 10 |

Note:
*[1]Sabouraud's agar medium was used.
*[2] & *[3]These compounds are stereoisomers.

The substituted imidazole derivatives are quite low in toxicity, and their LD50 values are more than 1000 mg/kg when determined by oral route to mice. Thus, they are useful as antifungal agents.

The N-substituted imidazole derivatives can be administered parenterally, orally or locally to warm-blooded animals and human beings in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 10 mg to 5 g for human beings.

Specific examples of the N-substituted imidazole derivatives are as follows:

1-[1,2-Epoxy-2-(2-chlorophenyl)-2-phenylethyl]-imidazole;

1-[1,2-Epoxy-2-(2,4-dichlorophenyl)-2-phenylethyl]imidazole;

1-[1,2-Epoxy-2,2-di(2,4-dichlorophenyl)ethyl]imidazole;

1-[1,2-Epoxy-2-(2,4-dichlorophenyl)propyl]imidazole;

1-[1,2-Epoxy-2-(2,4-dichlorophenyl)octyl]imidazole;

1-[1,2-Epoxy-2-phenyl-3-(2,4-dichlorophenyl)propyl]imidazole;

1-[1,2-Epoxy-2-(2-methylthiophenyl)-2-(4-fluorophenyl)ethyl]imidazole;

1-[1,2-Epoxy-2-(2-chlorophenyl)-2-(4-ethylphenyl)ethyl]imidazole;

1-[1,2-Epoxy-2-(2-chlorophenyl)-2-(4-isopropylphenyl)ethyl]imidazole;

1-[1,2-Epoxy-2-(2,4-dichlorophenyl)-2-(4-cyanophenyl)ethyl]imidazole;

1-[1,2-Epoxy-2-(2,4-dichlorophenyl)-2-(4-methylsulfonyloxyphenyl)ethyl]imidazole;

1-[1,2-Epoxy-2-(2-chlorophenyl)-2-(4-hydroxyphenyl)ethyl]imidazole;

1-[1,2-Epoxy-2-phenyl-2-(4-aminophenyl)ethyl]imidazole;

1-[1,2-Epoxy-2-phenyl-2-(4-acetylaminophenyl)ethyl]imidazole;

1-[1,2-Epoxy-2-phenyl-2-(4-dimethylaminophenyl)ethyl]imidazole.

Practical and presently preferred embodiments of the invention are illustratively shown in the following examples, which are not intended to limit the scope of the invention thereto.

EXAMPLE 1

Tri-n-butyltin imidazole (1.79 g) (prepared by the method as described in Rec. Trav. Chim., Vol. 81, 202 (1962)) and 1-(2-chlorophenyl)-1-phenyl-1-chloroacetaldehyde (660 mg) were dissolved in benzene (30 ml), and the mixture was heated under reflux for 5 hours. After cooling, the reaction mixture was washed with water, dried over anhydrous magnesium sulfate and evaporated to remove the solvent. The oily residue was purified by chromatography over silica gel to give 410 mg of 1-[1,2-epoxy-2-(2-chlorophenyl)-2-phenylethyl]imidazole as an oil. $n_D^{22}$ 1.6063. Yield, 55.5%.

EXAMPLE 2

To a solution of 1-(2,4-dichlorophenyl)-1-phenyl-1-bromoacetaldehyde (1.33 g) in acetonitrile (30 ml) was added imidazole (544 mg), and the mixture was stirred at room temperature for 3 hours. The reaction mixture was extracted with methylene chloride, and the extract was washed with water, dried and evaporated to remove the solvent. The oily residue was purified by chromatography over silica gel to give 1-[1,2-epoxy-2-(2,4-dichlorophenyl)-2-phenylethyl]imidazole (440 mg, yield 34%) melting at 135°–137° C.

Elementary analysis for $C_{17}H_{12}N_2Cl_2O$ (%): Calcd.: C, 60.63; H, 3.63; N, 8.46; Cl, 21.45; Found: C, 60.33; H, 3.40; N, 8.47; Cl, 21.82.

EXAMPLE 3

To a solution of 1,1-di(2,4-dichlorophenyl)-1-chloroacetaldehyde (310 mg) in acetonitrile (10 ml) was added imidazole (300 mg), and the mixture was heated under reflux for 5 hours. The reaction mixture was worked up in the same manner as in Example 2 and purified by chromatography over silica gel to give 1-[1,2-epoxy-2,2-di(2,4-dichlorophenyl)ethyl]imidazole (100 mg, yield 31%) as an oil.

EXAMPLE 4

A mixture of tri-n-butyltin imidazole (9.28 g), 2-chloro-2-(2,4-dichlorophenyl)propionaldehyde (4.75 g) and toluene (100 ml) was heated under reflux for 5 hours. After cooling, the reaction mixture was washed with water, dried over anhydrous magnesium sulfate and evaporated to remove the solvent. The oily residue was purified by chromatography over silica gel to give 1-[1,2-epoxy-2-(2,4-dichlorophenyl)propyl]imidazole (2.35 g, yield 43.7%) as an oil. The product was dissolved in ether, and the ether solution was neutralized by adding fuming nitric acid to give crystals of 1-[1,2-epoxy-2-(2,4-dichlorophenyl)propyl]-imidazole nitrate, which were recrystallized from methanol.

Yield, 2.48 g, 37.3%. M.P., 146°–148° C. Elementary analysis for $C_{12}H_{11}N_3O_4Cl_2$ (%):

Calcd.: C, 43.37; H, 3.31; N, 12.65; Found: C, 43.12; H, 3.49; N, 12.53.

EXAMPLE 5

A mixture of tri-n-butyltin imidazole (9.28 g), 2-chloro-2-(2,4-dichlorophenyl)octylaldehyde (6.15 g) and toluene (100 ml) was heated under reflux for 5 hours. After cooling, the reaction mixture was washed with water, dried over anhydrous magnesium sulfate and evaporated to remove the solvent. Since the oily residue showed two spots in thin layer chromatography, it was purified by column chromatography over silica gel.

One stereo-isomer of 1-[1,2-epoxy-2-(2,4-dichlorophenyl)octyl]imidazole, of which relative configuration is unknown, was obtained as an oil from the first fraction. Yield, 600 mg, 8.8%. The oil was dissolved in ether and added with oxalic acid to give the oxalate, which was recrystallized from methanol. M.P., 138°–140° C.

Elementary analysis for $C_{19}H_{22}N_2O_5Cl_2.H_2O$ (%): Calcd.: C, 51.00; H, 5.36; N, 6.26; Found: C, 51.33; H, 5.16; N, 6.41.

The other stereo-isomer was obtained from the third fraction as an oil. Yield, 800 mg, 11.8%. The oxalate was prepared in the same manner as above and recrystallized from isopropanol. M.P., 124°–127° C.

Elementary analysis for $C_{19}H_{22}N_2O_5Cl_2.H_2O$ (%): Calcd.: C, 51.00; H, 5.36; N, 6.26; Found: C, 51.24; H, 4.98; N, 6.27.

The second fraction gave a mixture of the stereoisomers as an oil. Yield, 1.34 g, 20.0%.

EXAMPLE 6

A mixture of tri-n-butyltin imidazole (3.0 g), 2-chloro-2-phenyl-3-(2,4-dichlorophenyl)propylaldehyde (1.5 g) and toluene (50 ml) was heated under reflux for 3 hours. After cooling, the solvent was evaporated off under reduced pressure from the reaction mixture to give an oily residue. The residue was purified by chromatography over silica gel to give 1-[1,2-epoxy-2-phenyl-3-(2,4-dichlorophenyl)propyl]-imidazole (yield, 580 mg, 35%) as an oil. The oil was dissolved in ether and added with fuming nitric acid to give the nitrate, which was recrystallized from methanol. M.P., 122°–124° C.

Elementary analysis for $C_{18}H_{15}N_3O_4Cl_2$(%): Calcd.: C, 52.94; H, 3.68; N, 10.29; Found: C, 53.15; H, 3.49; N, 10.46.

In the same manner as in Example 1, the following compounds were obtained:

1-(1,2-Epoxy-2,2-diphenylethyl)imidazole, M.P., 71°-73° C.;

1-[1,2-Epoxy-2,2-di(4-chlorophenyl)ethyl]imidazole, M.P., 103°-107° C.;

1-[1,2-Epoxy-2-(4-chlorophenyl)-2-phenylethyl]imidazole, $n_D^{22}$ 1.5978;

1-[1,2-Epoxy-2-(2-chlorophenyl)-2-(4-chlorophenyl)ethyl]imidazole, $n_D^{22}$ 1.5773;

1-[1,2-Epoxy-2-(2-chlorophenyl)-2-(4-chlorophenyl)ethyl]imidazole nitrate, M.P., 131°-133° C.;

1-[1,2-Epoxy-2-(2-chlorophenyl)-2-(4-fluorophenyl)ethyl]imidazole, $n_D^{22}$ 1.5786;

1-[1,2-Epoxy-2-(2-chlorophenyl)-2-(4-fluorophenyl)ethyl]imidazole nitrate, M.P., 162°-164° C.; 1-[1,2-Epoxy-2-(3-chlorophenyl)-2-(4-chlorophenyl)ethyl]imidazole, M.P., 85°-88° C.;

1-[1,2-Epoxy-2-(2,4-dichlorophenyl)-2-(4-chlorophenyl)ethyl]imidazole, M.P., 117°-119° C.;

1-[1,2-Epoxy-2-(2,4-dichlorophenyl)-2-(4-chlorophenyl)ethyl]imidazole nitrate, M.P. 115°-117° C.;

1-[1,2-Epoxy-2-(2,4-dichlorophenyl)-2-(4-chlorophenyl)ethyl]imidazole hydrochloride, M.P., 149°-153° C.;

1-[1,2-Epoxy-2-(2,4-dichlorophenyl)-2-(4-chlorophenyl)ethyl]imidazole oxalate, M.P., 150°-156° C.;

1-[1,2-Epoxy-2-phenyl-2-(4-nitrophenyl)ethyl]imidazole, M.P. 125°-130° C.;

1-[1,2-Epoxy-2-(2,4-dimethylphenyl)-2-phenyl-ethyl]imidazole nitrate, M.P., 149°-150° C.;

1-[1,2-Epoxy-2-(2,4-dichlorophenyl)-2-(2-chlorophenyl)ethyl]imidazole, M.P., 155°-158° C.;

1-[1,2-Epoxy-2-(2-chlorophenyl)-2-(p-biphenylylyl)-ethyl]imidazole oxalate, M.P., 104°-105° C.;

1-[1,2-Epoxy-2-(2-chlorophenyl)-2-(4-phenoxyphenyl)ethyl]imidazole oxalate, M.P., 92°-100° C.;

1-[1,2-Epoxy-2-(2,4-diiodophenyl)-2-phenylethyl]imidazole oxalate, M.P., 166°-169° C.;

1-[1,2-Epoxy-2-(2-iodophenyl)-2-(4-iodophenyl)-ethyl]imidazole oxalate, M.P., 78°-81° C.;

1-[1,2-Epoxy-2,2-di(2-chlorophenyl)ethyl]imidazole, M.P., 147°-149° C.;

1-[1,2-Epoxy-2-(2-chlorophenyl)-2-(3-trifluoromethylphenyl)ethyl]imidazole nitrate, M.P., 189° C.;

1-[1,2-Epoxy-2-(2-chlorophenyl)-2-(3-methoxyphenyl)ethyl]imidazole nitrate, M.P., 72°-80° C.;

1-[1,2-Epoxy-2-(4-chlorophenyl)-2-(4-methoxycarbonylphenyl)ethyl]imidazole, oily substance;

1-[1,2-Epoxy-2-(2-chlorophenyl)-2-(4-phenylthiophenyl)ethyl]imidazole, oily substance;

1-[1,2-Epoxy-2-(4-chlorophenyl)-2-(4-carboxyphenyl)ethyl]imidazole, M.P., 155°-160° C.;

1-[1,2-Epoxy-2-(4-chlorophenyl)-2-(4-carbamoylphenyl)ethyl]imidazole, M.P., 170°-175° C.;

1-[1,2-Epoxy-2-(2-chlorophenyl)-2-(4-N-acetylpiperazinophenyl)ethyl]imidazole, M.P., 76°-81° C.;

1-[1,2-Epoxy-2-(2,4-dibromophenyl)-2-phenylethyl]imidazole, M.P., 145°-147° C.;

1-[1,2-Epoxy-2-(2,4-difluorophenyl)-2-phenylethyl]imidazole oxalate, M.P., 165°-167° C.;

1-[1,2-Epoxy-2-(2-chloro-6-fluorophenyl)-2-phenylethyl]imidazole nitrate, M.P., 137°-138° C.;

1-[1,2-Epoxy-2-(2-chloro-6-fluorophenyl)-2-(4-chlorophenyl)ethyl]imidazole hydrochloride, M.P., 174°-180° C.;

1-[1,2-Epoxy-2-(2-chloro-6-fluorophenyl)-2-(4-chlorophenyl)ethyl]imidazole nitrate, M.P., 175°-178° C.;

1-[1,2-Epoxy-2-(2-chloro-6-fluorophenyl)-2-(4-chlorophenyl)ethyl]imidazole oxalate, M.P., 170°-172° C.

What is claimed is:

1. An N-substituted imidazole compound of the formula:

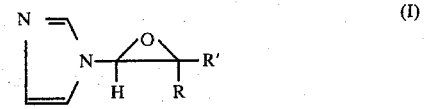

wherein R and R' are independently a phenyl group optionally substituted with one or more halogen, $C_1$-$C_8$ alkyl, $C_1$-$C_8$ alkoxy, $C_1$-$C_8$ alkylthio, phenyl, phenoxy, phenylthio, hydroxyl, trifluoromethyl, amino, carbamoyl, di($C_1$-$C_8$)alkylamino, $C_1$-$C_8$ alkanoylamino, nitro, cyano, carboxy, $C_1$-$C_8$ alkoxycarbonyl, $C_1$-$C_8$ alkylsulfonyloxy or $C_1$-$C_8$ alkanoylpiperazino groups; a $C_1$-$C_{15}$ alkyl group or a phenyl-($C_1$-$C_2$)alkyl group optionally bearing halogen on the benzene ring, and its acid-addition salts.

2. The compound according to claim 1, wherein R and R' are independently a phenyl group optionally substituted with one or more halogen, $C_1$-$C_8$ alkyl, $C_1$-$C_8$ alkoxy, $C_1$-$C_8$ alkylthio, phenyl, phenoxy, phenylthio, hydroxyl, trifluoromethyl, amino, carbamoyl, di($C_1C_8$)alkylamino, $C_1$-$C_8$ alkanoylamino, nitro, cyano, carboxy, $C_1$-$C_8$ alkoxycarbonyl, $C_1$-$C_8$ alkylsulfonyloxy or $C_1$-$C_8$ alkanoylpiperazino groups.

3. The compound according to claim 1, wherein R is a phenyl group optionally substituted with halogen and R' is a $C_1$-$C_{15}$ alkyl group or a phenyl($C_1$-$C_2$)alkyl group optionally bearing halogen on the benzene ring.

4. The compound according to claim 2, wherein R and R' are independently a phenyl group, a halophenyl group or a $C_1$-$C_8$ alkoxyphenyl group.

5. The compound according to claim 3, wherein R is a halophenyl group and R' is a $C_1$-$C_{15}$ alkyl group or a halobenzyl group.

6. The compound according to claim 4, wherein R is a 2,4-dichlorophenyl group and R' is a phenyl group.

7. The compound according to claim 4, wherein R is a 2,4-dibromophenyl group and R' is a phenyl group.

8. The compound according to claim 4, wherein R is a 2-chloro-6-fluorophenyl group and R' is a phenyl group.

9. The compound according to claim 4, wherein R is a 2-chlorophenyl group and R' is a 3-methoxyphenyl group.

10. The compound according to claim 4, wherein R is a 2-chlorophenyl group and R' is a 4-fluorophenyl group.

11. The compound according to claim 4, wherein R is a 2-chlorophenyl group and R' is a 4-chlorophenyl group.

12. The compound according to claim 4, wherein R is a 2-iodophenyl group and R' is a 4-iodophenyl group.

13. The compound according to claim 4, wherein R is a 2-chloro-6-fluorophenyl group and R' is a 4-chlorophenyl group.

14. The compound according to claim 4, wherein R is a 2,4-dichlorophenyl group and R' is a 2-chlorophenyl group.

15. The compound according to claim 4, wherein R is a 2,4-dichlorophenyl group and R' is a 4-chlorophenyl group.

16. The compound according to claim 4, wherein R and R' are both a 2,4-dichlorophenyl group.

17. The compound according to claim 5, wherein R is a 2,4-dichlorophenyl group and R' is an n-hexyl group.

18. An antifungal composition which comprises an antifungally effective amount of the N-substituted imidazole compound or its acid-addition salt as claimed in claim 1 as an active ingredient and a pharmaceutically acceptable carrier or diluent.

* * * * *